(12) United States Patent
Kusunoki

(10) Patent No.: US 7,582,860 B2
(45) Date of Patent: Sep. 1, 2009

(54) METHOD OF MEASURING AMOUNT OF MISSED TISSUE AT CHEST WALL SIDE AND PHANTOM

(75) Inventor: Tetsurou Kusunoki, Kanagawa-ken (JP)

(73) Assignee: FUJIFILM Corporation, Tokyo (JP)

( * ) Notice: Subject to any disclaimer, the term of this patent is extended or adjusted under 35 U.S.C. 154(b) by 27 days.

(21) Appl. No.: 11/780,557

(22) Filed: Jul. 20, 2007

(65) Prior Publication Data
US 2008/0019475 A1 Jan. 24, 2008

(30) Foreign Application Priority Data
Jul. 20, 2006 (JP) ............................. 2006-198323

(51) Int. Cl.
*G01D 18/00* (2006.01)
(52) U.S. Cl. .................................. 250/252.1
(58) Field of Classification Search ................ 250/252, 250/1; 378/207
See application file for complete search history.

(56) References Cited

U.S. PATENT DOCUMENTS

| 7,203,274 | B2 * | 4/2007 | Charles et al. ............... 378/54 |
| 2003/0072417 | A1 * | 4/2003 | Kaufhold et al. ............ 378/207 |
| 2006/0072706 | A1 * | 4/2006 | Russell ........................ 378/162 |
| 2007/0110665 | A1 * | 5/2007 | Bolan et al. ................. 424/1.11 |

FOREIGN PATENT DOCUMENTS

| JP | 2004-154409 |   | 6/2004 |
| JP | 2004-298617 | A | 10/2004 |
| JP | 2005-058315 | A | 3/2005 |
| JP | 2005-296343 | A | 10/2005 |

OTHER PUBLICATIONS

Bloomquist et al., "Quality control for digital mammography in the ACRIN DMIST trial: Part 1," Medical Physics, vol. 33, No. 3, Mar. 23, 2006, pp. 719-736, XP-012092037.
Sunnybrook Health Sciences Centre: "The MISTY Phantom," XP-002458369, retrieved from the Internet: URL:http://66.59.179.35/research/groups/dm/projects/phantom_dev/misty>, retrieved Nov. 12, 2007, 2 pages.
Sunnybrook Health Sciences Centre: "Tissue Missed at the Chest Wall," XP-002458370, retrieved from the Internet: URL:http://66.59.179.35/research/groups/dm/projects/phanton_dev/misty/missued_tissue>, retrieved Nov. 12, 2007, 1 page.

(Continued)

*Primary Examiner*—David P Porta
*Assistant Examiner*—Kiho Kim
(74) *Attorney, Agent, or Firm*—Sughrue Mion, PLLC

(57) ABSTRACT

A phantom is provided with: a reference marker at a predetermined position thereof; a positioning reference surface, to be placed into contact with a chest wall abutting surface of a support table of a mammography apparatus; and a pattern region for measuring distances from the reference surface, perpendicular to the reference surface. The amount of transmitted radiation changes within the pattern region in a direction perpendicular to the reference surface according to a predetermined rule. The phantom is placed on the support table to measure the amount of chest wall loss.

9 Claims, 11 Drawing Sheets

OTHER PUBLICATIONS

Pehamed: "The DINo 152, 7 phantom," May 13, 2005, XP-002458371, retrieved from the Internet: URL:http://web.archive.org/web/20050513012505/www.pehamed.de/get_image.php?IMAGEID=153&DIM=0>, retrieved Nov. 12, 2007, 2 pages.

Ryuji Suzuki et al., "Academic Publication of Radiation Medicine and Technology 14-3; Mammography Accuracy Management Manual (Revision 3)," Japanese Society of Radiological Technology, Dec. 28, 2004, pp. 78-80 and a partial translation thereof.

* cited by examiner

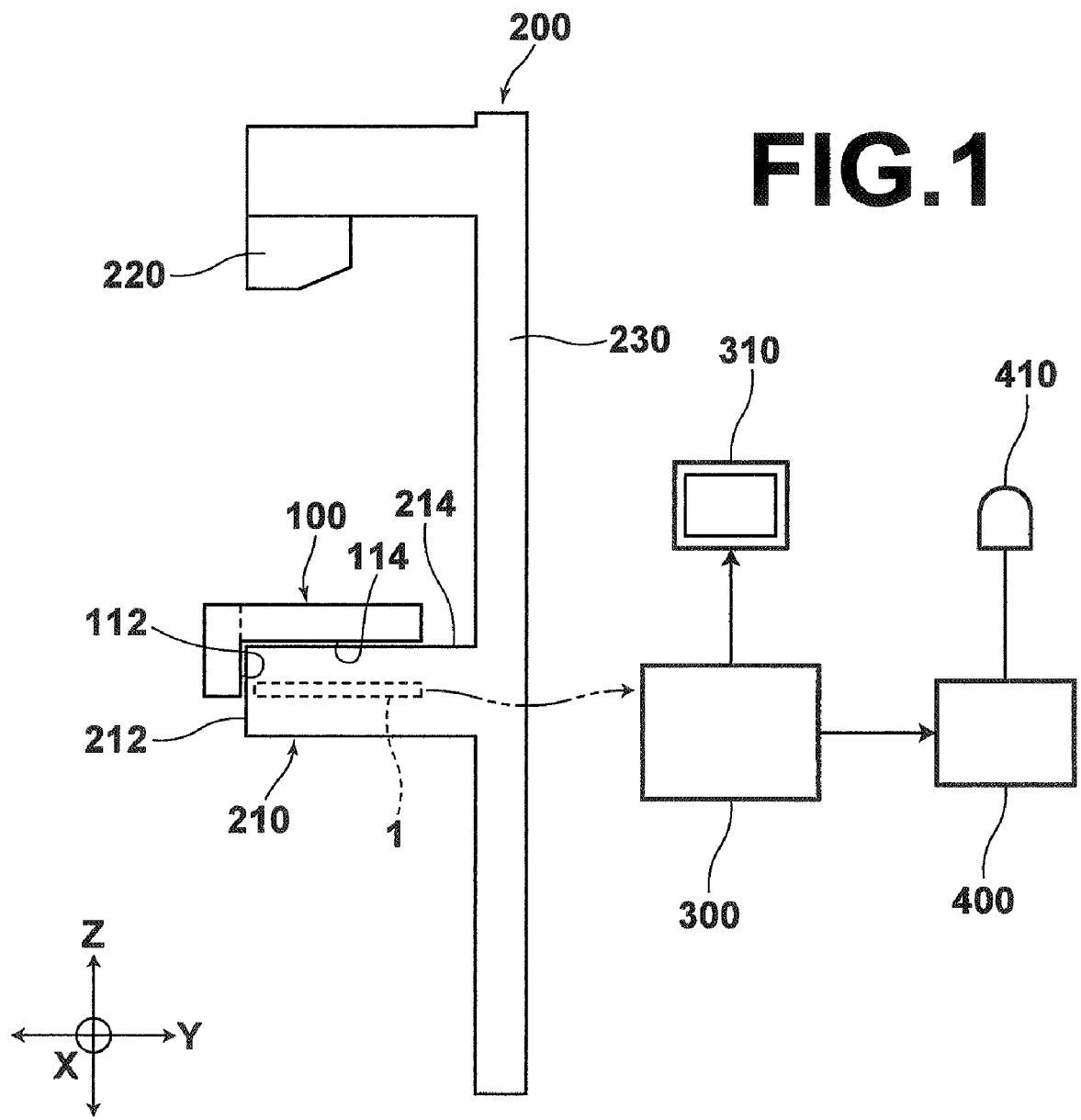

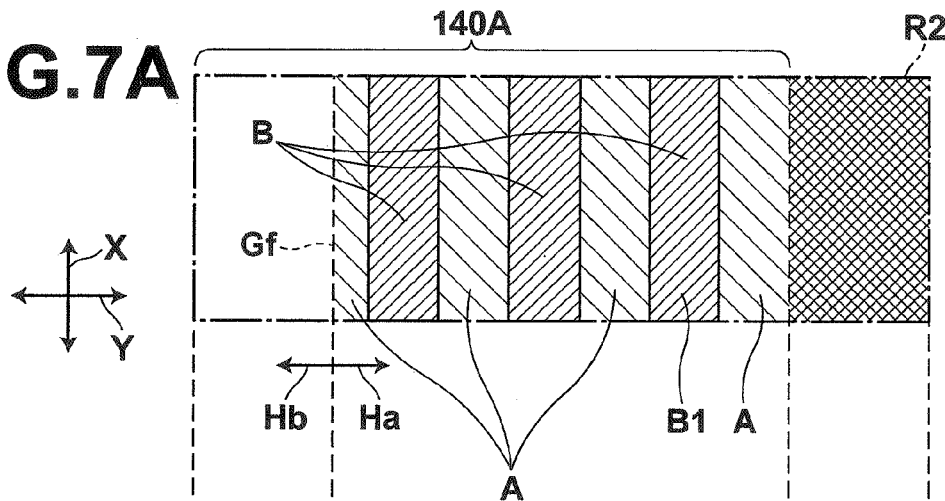
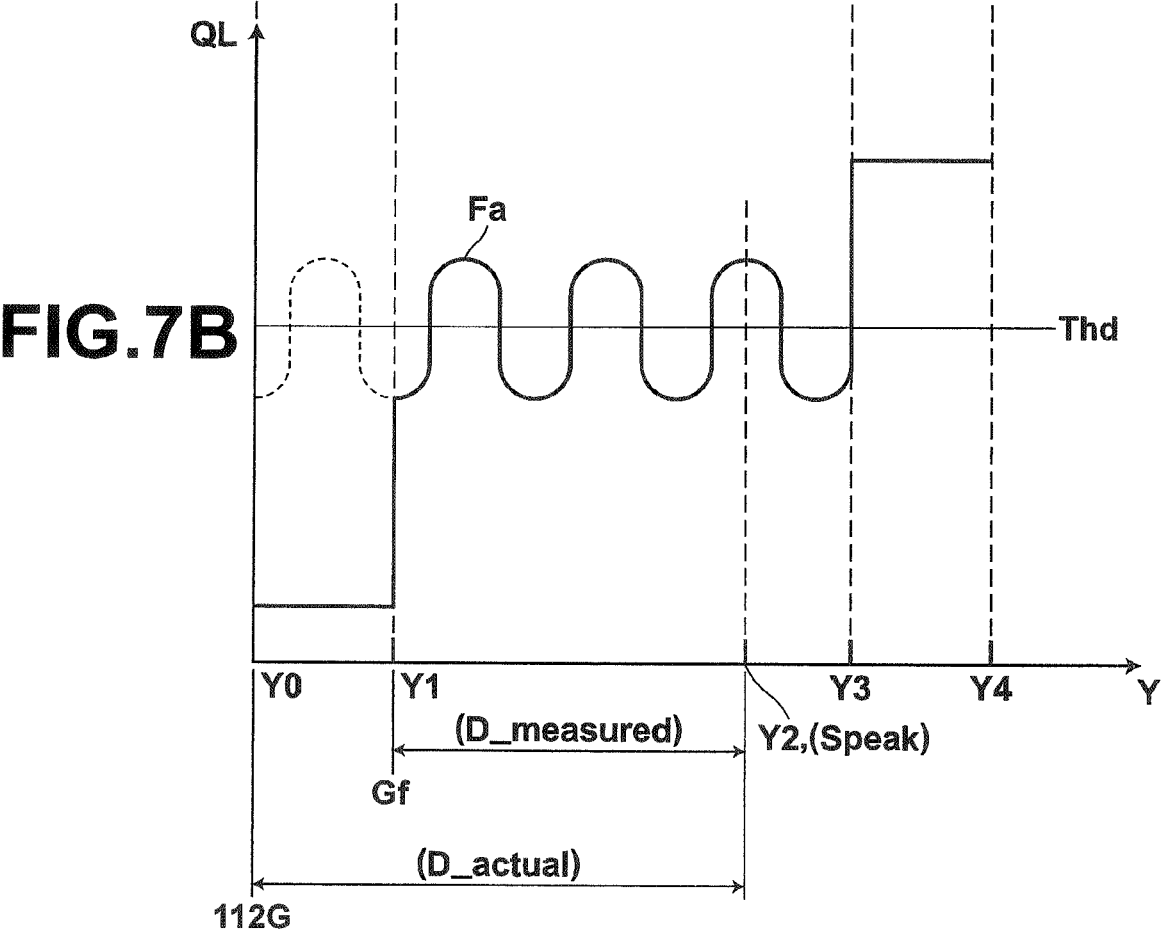

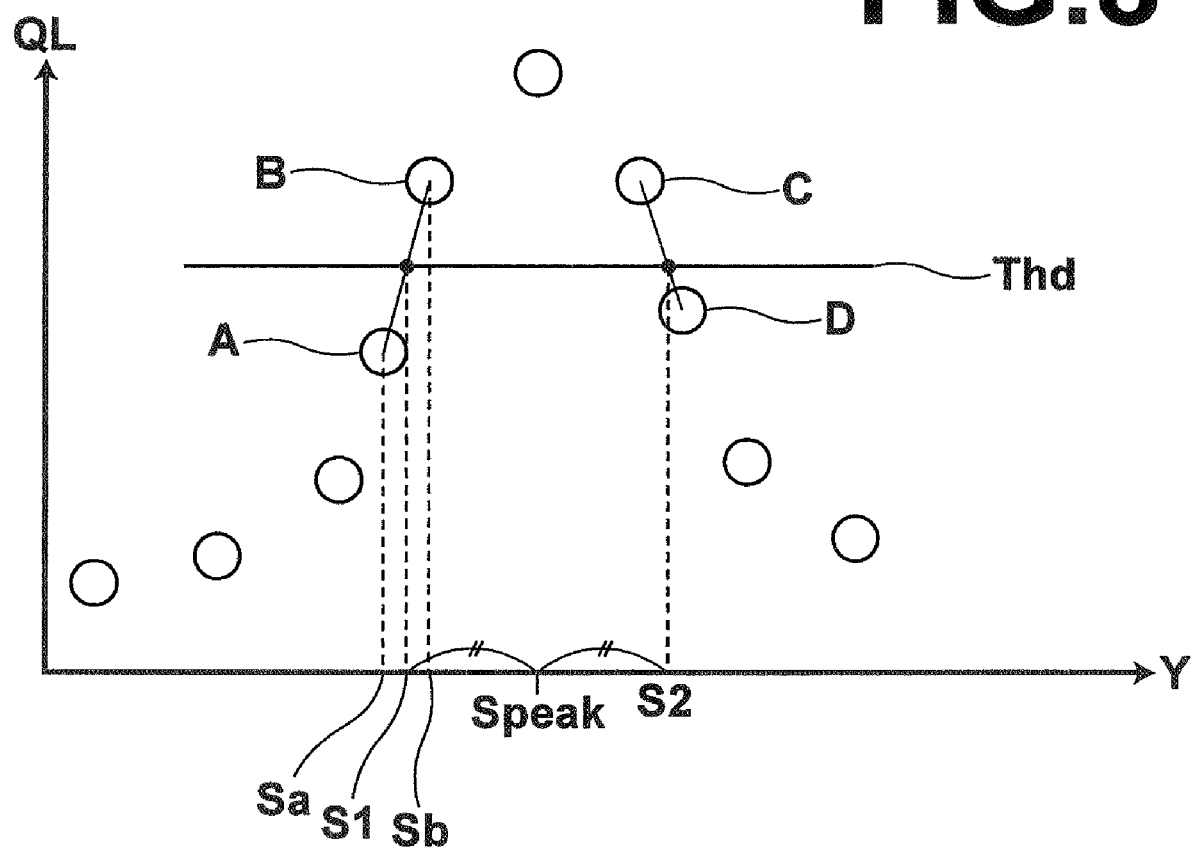

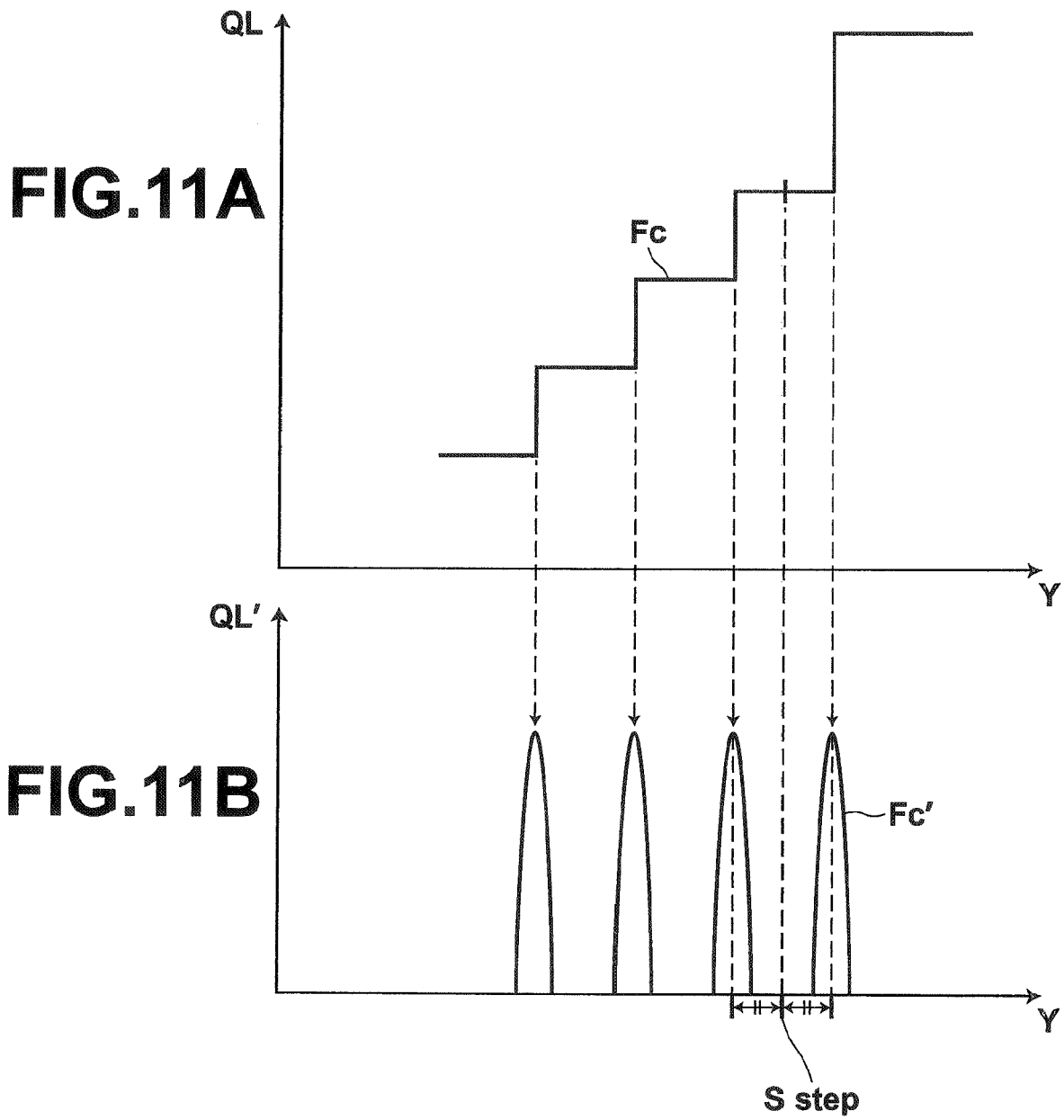

METHOD OF MEASURING AMOUNT OF MISSED TISSUE AT CHEST WALL SIDE AND PHANTOM

BACKGROUND OF THE INVENTION

1. Field of the Invention

The present invention relates to a method of measuring an amount of missed tissue at chest wall side by placing a phantom on a support table for breast radiography and to a phantom used in this method.

2. Description of the Related Art

Apparatuses for radiographing and reading radiographic images are known in the field of medicine. In an apparatus of this kind, radiation emitted from a radiation source and carrying a radiographic image of a subject after passing the subject is irradiated on a radiographic image conversion panel to record the radiographic image of the subject on the panel, and the radiographic image is obtained by reading the radiographic image conversion panel. As such a radiographic image conversion panel, there is a known panel that stores a portion of energy of radiation emitted thereon and emits light with intensities corresponding to the stored radiation energy upon exposure to stimulating ray such as visible light. There is another known panel that temporarily stores electric charges generated by exposure to radiation in an electric charge storage unit of a solid state detection device and outputs the stored charge after converting the charges into an image signal.

In addition, a breast radiography apparatus that radiographs and reads a radiographic image of a breast is known as a type of radiography apparatus (see Japanese Unexamined Patent Publication No. 2004-154409). In the breast radiography apparatus, a breast of a subject is fixed on a support table having a radiographic image conversion panel installed therein, and radiation is emitted from a radiation source above the support table, to record the radiographic image of the breast in the panel.

The support table has a surface that is in contact with a chest wall of the subject (hereinafter referred to as the chest wall side) at the time of radiography. The breast radiography apparatus is set to irradiate the radiation from the radiation source as close as possible to the chest wall but not on the chest wall. In other words, the positional relationship between the radiation source and the support table is adjusted so as to cause the radiation from the radiation source to be emitted as close as possible to the chest wall side but not beyond the chest wall side. The radiographic image of the breast including an area close to the chest wall can therefore be obtained by this adjustment.

The positional relationship between the support table and the radiation source is basically fixed. However, this relationship may change due to various reasons, and a radiation field on the support table, that is, a region of radiography, needs to be measured occasionally. As a method of measuring deviations in the region of radiography, a method using a phantom is known. In this method, the distance between a chest wall side of a support table and an edge of a radiography region, that is, an amount of missed tissue at chest wall side, is measured by use of a phantom.

As a phantom used in this method, a phantom having iron balls having diameters of 2 mm aligned in one direction in a block is known (see Ryuji Suzuki et al., "Academic Publication of Radiation Medicine and Technology 14-3; Mammography Accuracy Management Manual (Revision 3)", Publication Committee of Japanese Society of Radiological Technology, Dec. 28, 2004, pp. 78-80). The iron balls are aligned so as to be perpendicular to a chest wall side when the phantom is placed on a support table.

The amount of missed tissue at chest wall side can be obtained by radiographing the phantom in a state where a reference surface of the phantom is in contact with a chest wall side of a support table. In other words, by counting how many iron balls aligned in one line have been radiographed or not radiographed in a radiographic image, the amount of missed tissue at chest wall side representing the distance between the chest wall side to an edge of a radiography region can be found.

In measurement of an amount of missed tissue at chest wall side by using the phantom having the iron balls aligned in one direction, an image representing the iron balls radiographed and displayed by a breast radiography apparatus is visually evaluated. However, measurement accuracy is not sufficient only by viewing in this manner, and there is demand for measurement of an amount of missed tissue at chest wall side with higher accuracy.

SUMMARY OF THE INVENTION

The present invention has been conceived based on consideration of the above circumstances, and an object of the present invention is to provide a method that can improve measurement accuracy of an amount of missed tissue at chest wall side and a phantom used in this method.

A phantom of the present invention is a phantom placed on a support table for breast radiography and used for measurement of an amount of missed tissue at chest wall side, and the phantom comprises:

a reference marker located at a predetermined position in the phantom;

a reference surface for positioning, to be placed in contact with a chest wall side of the support table; and a pattern region that is used for measurement of a distance from the reference surface and is formed by a region wherein the amount of transmitted radiation changes in a direction perpendicular to the reference surface according to a predetermined rule.

The pattern region for distance measurement can be a region wherein the amount of transmitted radiation decreases or increases monotonically. Alternatively, the pattern region may be a region wherein the amount of transmitted radiation changes in a stepwise manner.

The reference marker may have any form as long as the marker can be recorded by radiograph (the details thereof will be described later).

A method of the present invention for measuring an amount of missed tissue at chest wall side uses a phantom that is placed on a support table for breast radiography and is used for measurement of the amount of missed tissue at chest wall side. The phantom comprises a reference marker located at a predetermined position in the phantom, a reference surface for positioning, to be placed in contact with a chest wall side of the support table, and a pattern region that is formed by a region wherein amount of transmitted radiation used for measurement of a distance from the reference surface shows periodic changes, monotonic decrease or increase, or stepwise change in a direction perpendicular to the reference surface according to a predetermined rule. The method comprises the steps of:

placing the phantom on the support table;

recording a radiation image of the phantom in a radiation image conversion panel placed in the support table while radiographing the phantom;

obtaining base image data representing a base radiation image of the phantom including the reference marker by performing readout of the radiation image conversion panel;

finding a magnification ratio and a position of the phantom from a test radiation image obtained by further radiography of the phantom and from a position of the reference marker recorded in the test radiation image;

determining a calculation region corresponding to the pattern region in the test radiation image, based on the position of the phantom and the base image data;

finding the number of repetitions and/or the amount of change in the amount of transmitted radiation in the calculation region according to the predetermined rule; and finding the amount of missed tissue at chest wall side from the number of repetitions and/or the amount of the change.

The method of the present invention for measuring the amount of missed tissue at chest wall side may further comprise the steps of:

comparing the amount of missed tissue at chest wall side with a predetermined permitted amount of missed tissue at chest wall side; and issuing a warning in the case where the amount of missed tissue at chest wall side has been judged to exceed the permitted amount of missed tissue at chest wall side.

In the method of the present invention for measuring the amount of missed tissue at chest wall side, the phantom having the reference marker and the pattern region for measuring distances from the reference surface is placed on the support table used for breast radiography, and the radiation image of the phantom is radiographed and recorded in the radiation image conversion panel placed in the support table. The base image data representing the base radiation image of the phantom including the reference marker are obtained by performing readout of the radiation image conversion panel. The magnification ratio is found from the test radiation image obtained by further radiography of the phantom thereafter while the position of the phantom is detected by the position of the reference marker recorded in the test radiation image. Based on the detected position of the phantom, the calculation region corresponding to the distance measurement pattern region is determined in the test radiation image, and the number of repetitions and/or the amount of the change in amount of transmitted radiation is/are found in the calculation region according to the predetermined rule. Based on the number of repetitions and/or the amount of the change, the amount of missed tissue at chest wall side is found. Therefore, the amount of missed tissue at chest wall side can be measured with higher accuracy than conventional measurement thereof by visual examination. In other words, since the amount of missed tissue at chest wall side is calculated by image processing of the radiation image obtained by radiography of the phantom, the amount can be found with higher accuracy. In addition, by storing the amount of missed tissue at chest wall side having been calculated, temporal change in the amount can be easily understood and managed.

In the method described above, if the amount of missed tissue at chest wall side is compared with the permitted amount of chest wall loss and the warning is issued in the case where the amount has been judged to exceed the permitted amount, the amount of missed tissue at chest wall side can be managed with more certainty.

Since the phantom of the present invention comprises the reference marker located at the predetermined position in the phantom, the positioning reference surface to be placed in contact with the chest wall side of the support table, and the pattern region that is used for measurement of the distance from the reference surface and is formed by the region wherein the amount of transmitted radiation changes in the direction perpendicular to the reference surface according to the predetermined rule, the phantom enables measurement of the amount of missed tissue at chest wall side with high accuracy by being used in the above method.

BRIEF DESCRIPTION OF THE DRAWINGS

FIG. 1 shows the configuration of a quality control system for missed tissue at chest wall side by which a method of the present invention for measuring an amount of missed tissue at chest wall side is carried out;

FIG. 2A is a plan view from the above of the phantom placed on a support table while FIG. 2B is a side view of the phantom placed on the support table;

FIG. 3A shows a magnification ratio calculation region including images of linear components while FIG. 3B shows profile data obtained by averaging pixel values along an X direction;

FIG. 4A shows positions of the phantom and the calculation region in a base radiation image relative to the radiation image conversion panel while FIG. 4B shows positions of the phantom and the calculation region in a test radiation image relative to the radiation image conversion panel;

FIG. 5A shows the calculation region while FIGS. 5B and 5C respectively show an image represented by averaged pixel values representing a one-dimensional region and the profile data thereof;

FIG. 6A shows an image of the phantom in a base radiation image Go while FIG. 6B shows an image of the phantom in a test radiation image Gk;

FIGS. 7A and 7B show how the amount of missed tissue at chest wall side is found by using a distance measurement pattern in which the amount of transmitted radiation changes periodically, and FIG. 7A shows a calculation region including a pattern image representing the distance measurement pattern while FIG. 7B shows periodically changing profile data;

FIG. 8 shows how a center position of an image representing a radiation blocking component is calculated;

FIG. 9A shows a calculation region including an image of the distance measurement pattern while FIG. 9B shows monotonically increasing profile data;

FIG. 10A shows a calculation region including an image of the distance measurement pattern while FIG. 10B shows stepwise profile data; and FIGS. 11A and 11B show how a center position of a step is found by differentiation of the stepwise profile data, and FIG.

11A shows the stepwise profile data before differentiation while FIG. 11B shows differentiated stepwise profile data.

DESCRIPTION OF THE PREFERRED EMBODIMENT

Figure 2A:
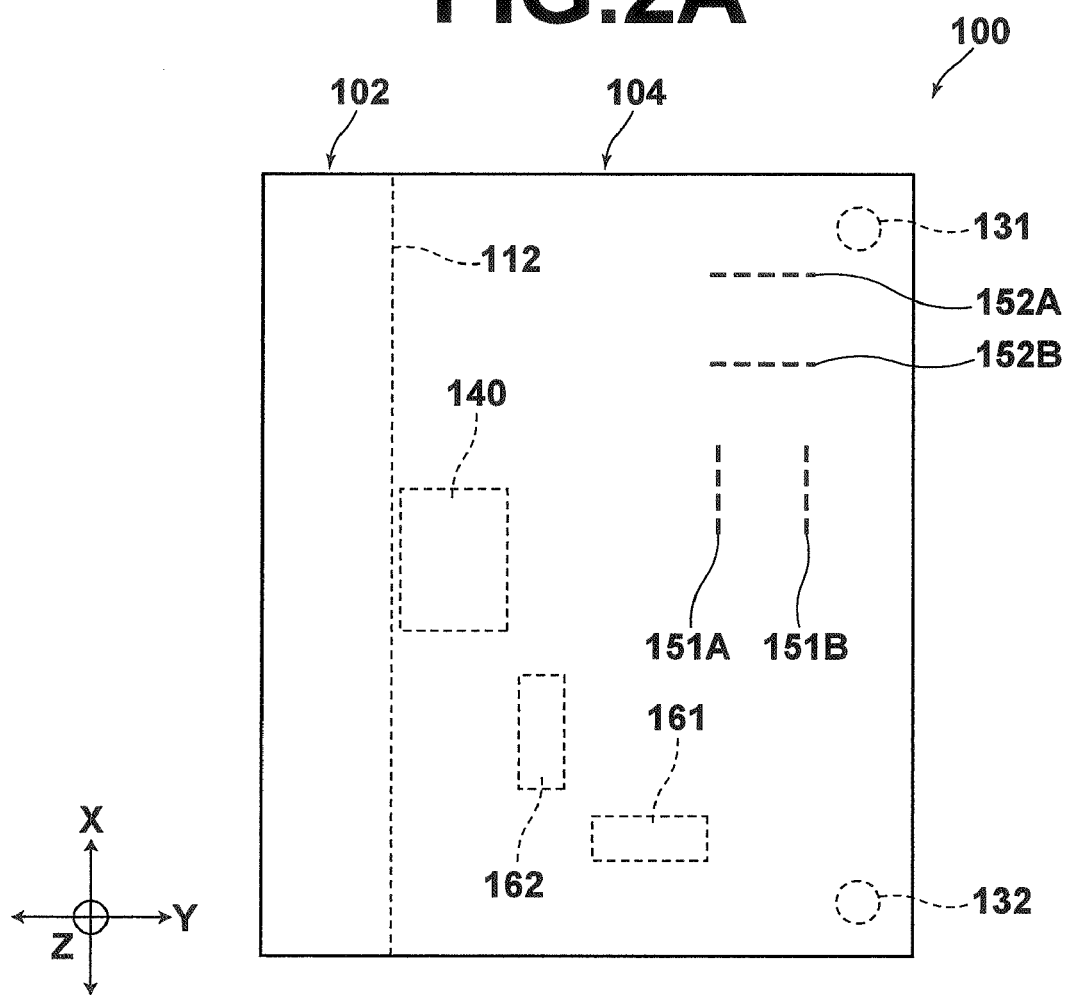
FIGS. 2A and 2B show a phantom used in the method of the present invention.
Figure 2B:
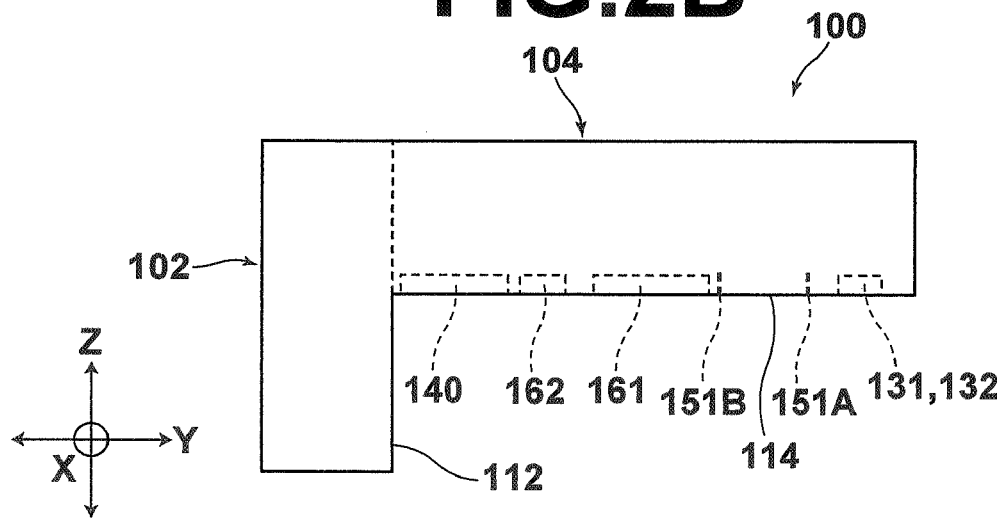

Hereinafter, an embodiment of the present invention will be described with reference to the accompanying drawings. FIG. 1 shows the configuration of a quality control system for missed tissue at chest wall side (hereinafter simply referred to as the quality control system) by which a method of the present invention for measuring an amount of missed tissue at chest wall side (hereinafter referred to as the missed tissue at chest wall side measurement method) is carried out. FIGS. 2A and 2B show a phantom used in the method. FIG. 2A is a plan view from the above of the phantom placed on a support table while FIG. 2B is a side view of the phantom.

The quality control system automatically measures and manages the amount of missed tissue at chest wall side by radiographing the phantom. Hereinafter, the configuration of the quality management system for measuring the amount of missed tissue at chest wall side will be described in detail.

The quality control system shown in FIG. 1 comprises a breast radiography apparatus 200 for carrying out radiography of a breast, a radiation image reading apparatus 300 for reading image data representing a radiation image radiographed by the apparatus 200 and recorded in a radiation image conversion panel 1, a display device 310 for displaying the radiation image by input of the image data thereto, an apparatus 400 for calculation of the amount of missed tissue at chest wall side (hereinafter referred to as the missed tissue at chest wall side calculation apparatus 400) based on the image data, and a comparing warning apparatus 410 for comparing the calculated amount of missed tissue at chest wall side with a predetermined permitted amount of missed tissue at chest wall side and for issuing a warning in the case where the calculated amount has been judged to exceed the permitted amount.

The breast radiography apparatus 200 comprises a support table 210 that supports a breast for radiography, a radiation source 220 that is located above the support table and emits radiation (such as X rays), and a support column 230 to which the support table 210 and the radiation source 220 are fixed so as to maintain a constant positional relationship between the support table and the source.

The radiation image conversion panel 1 is located inside the support table 210. The radiation emitted from the radiation source 220 passes the breast placed on the support table 210 and is irradiated on the panel 1 to record the radiation image of the breast in the panel.

The radiation image recorded in the radiation image conversion panel 1 is read by the radiation image reading apparatus 300, and displayed on the display device 310.

As shown in FIGS. 2A and 2B, the phantom 100 is used for measuring the amount of missed tissue at chest wall side by being placed on the support table 210 of the breast radiography apparatus 200. The phantom 100 comprises reference markers 131 and 132 at predetermined positions therein, a reference surface 112 for positioning that is to be in contact with a chest wall side 212 of the support table 210, and a distance measurement pattern region 140 that is formed by a region in which amount of transmitted radiation changes in a direction perpendicular to the reference surface 112 according to a predetermined rule and is used for measurement of a distance from the reference surface 112.

The distance measurement pattern region 140 may be a region wherein the amount of transmitted radiation changes periodically, or decreases or increases monotonically, or changes in a stepwise manner.

More specifically, the phantom 100 comprises a reference region 102 having a shape of rectangular solid in which the reference surface 112 is formed, and a support region 104 having a shape of rectangular solid starting from the reference region 102 and perpendicular to the reference surface 112. The distance measurement pattern region 140 is formed in the support region 104.

The phantom 100 is radiographed in a state where the reference surface 112 thereof is in contact with the chest wall side 212 that is perpendicular to an upper surface 214 of the support table 210 while a lower surface 114 of the support region 104 thereof is placed on the upper surface 214 of the support table 210. Ideally, positions of the reference surface 112 and the chest wall side 212 agree with each other, and the reference surface 112 of the phantom 100 is perpendicular to the lower surface 114.

The chest wall side 212 of the support table 210 is a surface that is perpendicular to a direction shown by a two-direction arrow Y (hereinafter referred to as the Y direction) in FIG. 1 while the upper surface 214 thereof is perpendicular to a direction shown by a two-direction arrow Z (hereinafter referred to as the Z direction) in FIG. 1. A direction represented by X (hereinafter referred to as the X direction) in FIG. 1 is parallel to the chest wall side 212 and the upper surface 214. Therefore, if the phantom 100 is placed in a proper manner on the support table 210, the reference surface 112 and the lower surface 114 thereof are respectively perpendicular to the Y direction and to the Z direction in FIG. 1 while the X direction in FIG. 1 is parallel to the surfaces 112 and 114.

The directions shown by X, Y, and Z are perpendicular to each other.

The distance measurement pattern region 140 can be formed by cutting a base material of the support region 104, which is a part of the phantom 100, or by combining two or more types of materials. The pattern region 140 has a geometric structure for forming a predetermined radiation image on the radiation image conversion panel 1.

More specifically, the materials comprising the phantom 100 may be a combination of the base material comprising a resin such as an acrylic resin and a metal material such as iron, stainless steel, aluminum, or copper having a different radiation transmittance from the base material. For example, an acrylic resin may be adopted as the base material comprising the phantom 100 while aluminum may be used as the material comprising the pattern region 140 and the reference markers 131 and 132.

The reference markers 131 and 132 are formed by slightly carving or completely cutting the base material of the support region 104 in the phantom 100 in the form of circles, or by placing circular components, that is, circular plates whose radiation transmittance is different from the base material. The reference markers 131 and 132 are placed so as to cause a direction of thickness of the plates is perpendicular to the lower surface 114 of the phantom 100. Square plates may be used as the reference materials 131 and 132, instead of the circular plates.

Linear components 151A and 151B are positioned in the support region 104 of the phantom 100, for finding a magnification ratio of an image of the phantom 100 recorded in the radiation image conversion panel 1 through radiography of the phantom. The linear components 151A and 151B are used to find the magnification ratio along the Y direction, and the components are parallel to the X direction with a known interval in the Y direction between the components.

Linear components 152A and 152B are positioned in the support region 104 of the phantom 100, for finding a magnification ratio in the X direction that is different from the Y direction. The linear components 151A and 151B are used to find the magnification ratio in the X direction, and the components are parallel to the Y direction with a known interval in the X direction between the components.

The magnification ratio is a ratio of a size of the radiation image radiographed and read by radiography of the phantom to an actual size of the phantom 100. This ratio includes an effect that the radiation image of the phantom 100 is enlarged upon projection of the image onto the radiation image conversion panel 1 during recording.

A rectangular piece 161 wherein a distance between two sides thereof in the Y direction is known and a rectangular piece 162 wherein a distance between two sides thereof in the X direction is known may be placed on the support region 104 as components for calculating the magnification ratio. The components for magnification ratio calculation are components whose radiation transmittance is different from that of the base material. Alternatively, a part of the material comprising the distance measurement pattern region 140, such as one end and another end thereof, may also be used as a component for magnification ratio calculation.

It is preferable for a part of surfaces of the phantom 100 touched by a user to have been subjected to antimicrobial processing. A resin comprising the phantom 100 may be biodegradable. Alternatively, the phantom may be used while being covered with an antimicrobial sheet.

It is preferable of an adhesive that hardly generates an uneven image and has a higher radiation transmittance to be used as a method of fixing the components on the phantom 100.

Hereinafter, the missed tissue at chest wall side measurement method carried out by the quality control system having the above configuration will be described.

The method of the present invention comprises the steps of: 1. acquisition of base data of a phantom position, 2. calculation of the magnification ratio, 3. detection of a phantom position, 4. setting a calculation region, and 5. calculation of the amount of missed tissue at chest wall side. Further, step 6. judgment of the amount of missed tissue at chest wall side may also be included.

More specifically, in this method, the phantom 100 is placed on the support table 210 of the breast radiography apparatus 200 and radiographed by the apparatus 200. A radiation image of the phantom 100 is recorded in the radiation image conversion panel 1 in the support table 210, and the panel 1 is read by the radiation image reading apparatus 300 for obtaining base image data representing a base radiation image of the phantom 100 including the reference markers 131 and 132.

The magnification ratio is found from a test radiation image obtained by further radiography of the phantom 100 thereafter, and the position of the phantom 100 is detected from positions of the reference markers 131 and 132 recorded in the test radiation image.

The calculation region corresponding to the distance measurement pattern region 140 in the test radiation image is then determined, based on the position of the phantom 100 with respect to the radiation image conversion panel 1 detected in the test radiation image, and the position of the phantom 100 with respect to the radiation image conversion panel 1 detected by utilizing the positions of the reference markers 131 and 132 recorded in the base radiation image.

The amount of missed tissue at chest wall side is found by finding the number of repetitions and/or the amount of change in the amount of transmitted radiation according to the predetermined rule in the calculation region.

In radiography of the phantom, the radiation image conversion panel 1 is at all times placed at a predetermined position on the support table 210 without an error. Therefore, a positional relationship between the support table 210 and the radiation image conversion panel 1 is constant. Consequently, by finding positions of the reference markers 131 and 132 relative to an outline of edges of the radiation image conversion panel 1 in the radiation image read by the radiation image reading apparatus 300, the position of the phantom 100 or the like relative to the chest wall side 212 of the support table 210 can be found, for example.

The magnification ratio, the position of the phantom 100, the calculation region, the amount of missed tissue at chest wall side, and the like are found by the missed tissue at chest wall side calculation apparatus 400 to which the image data read by the radiation image reading apparatus 300 have been input.

The calculation region is set in the following manner. The positions of the reference markers 131 and 132 corresponding to the image of the radiation image conversion panel 1 in the base radiation image are different from positions of the reference markers 131 and 132 relative to the image of the radiation image conversion panel 1 in the test radiation image by a deviation corresponding to an error in positioning of the phantom 100 on the support table 210 at the time of radiography of the test radiation image. Therefore, by shifting a correct calculation region predetermined for an image of the distance measurement pattern formed in the phantom 100 in the base radiation image by the deviation, the calculation region can be found in the test radiation image.

In the missed tissue at chest wall side measurement method, the comparing warning apparatus 410 compares the amount of missed tissue at chest wall side with the predetermined permitted amount of missed tissue at chest wall side, and carries out warning in the case where the amount has been judged to exceed the permitted amount.

The missed tissue at chest wall side measurement method described above has the following advantages.

By radiographing the phantom, the amount of missed tissue at chest wall side can be automatically calculated from a radiation image of the geometric structure (the distance measurement pattern region) formed on a side of chest wall.

Through visual evaluation of the amount of missed tissue at chest wall side by displaying on a film or display the radiation image representing the geometric structure having been radiographed and recorded, judgment can also be made as to whether the positional relationship between the support table and the radiation source of the breast radiography apparatus is within a permitted range.

The state of missed tissue at chest wall side can be managed by setting a standard value of missed tissue at chest wall side for judgment regarding a permitted range and by comparing the measured amount of missed tissue at chest wall side with the standard value.

The standard value can be set freely according to a usage environment.

By managing history of measurement of missed tissue at chest wall side with a computer or the like, temporal change in the missed tissue at chest wall side can be easily understood.

Hereinafter, procedures of carrying out the missed tissue at chest wall side measurement method will be described in detail.

<Step 1: Acquisition of Base Data of Reference Phantom Position>

[Purpose]

If the phantom is not placed accurately on the support table, the amount of missed tissue at chest wall side cannot be measured correctly. Therefore, a correct position at which the phantom should be placed is found in advance, and processing for correcting the error regarding the phantom position needs to be carried out before acquisition of the amount of missed tissue at chest wall side. Consequently, base data acquisition is intended.

The base data acquisition is carried out only at the time of introduction of the quality control system.

[Procedures]

(1) At the time of introduction of the system, the phantom 100 is correctly placed on the support table 210. In other words, the reference surface 112 of the phantom 100 is correctly in contact with the chest wall side 212 of the support table 210 without a deviation in position.

(2) In the state of (1) described above, radiation is emitted from the radiation source 220, and a radiation image of the phantom 100 is recorded in the radiation image conversion panel 1. The radiation image reading apparatus 300 reads the radiation image recorded in the radiation image conversion panel 1, and obtains image data comprising digital values representing the outline of the radiation image conversion panel 1 and the radiation image of the phantom 100. In this manner, the base image data representing the base radiation image are obtained.

(3) According to a reference marker position detection algorithm, coordinates of the reference markers 131 and 132 are found by use of the image data, and stored in the missed tissue at chest wall side calculation apparatus 400. The coordinates can be found as coordinates representing the positions of the reference markers 131 and 132 relative to the outline of the radiation image conversion panel 1.

Let the coordinates of the reference markers 131 and 132 be denoted by (Mol, Sol) and (Mor, Sor), respectively.

The method described in paragraphs 0065 to 0089 in Japanese Unexamined Patent Publication No. 2004-298617 may be used as the reference marker position detection algorithm.

<Step 2: Calculation of Magnification Ratio>

Figure 3A:
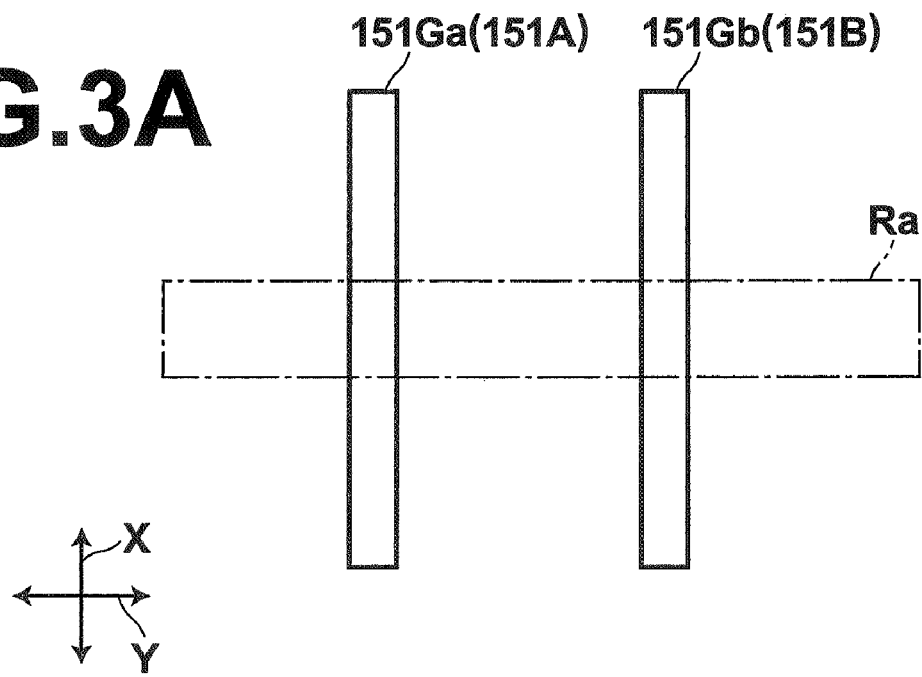
FIGS. 3A and 3B show how a magnification ratio is calculated.
Figure 3B:
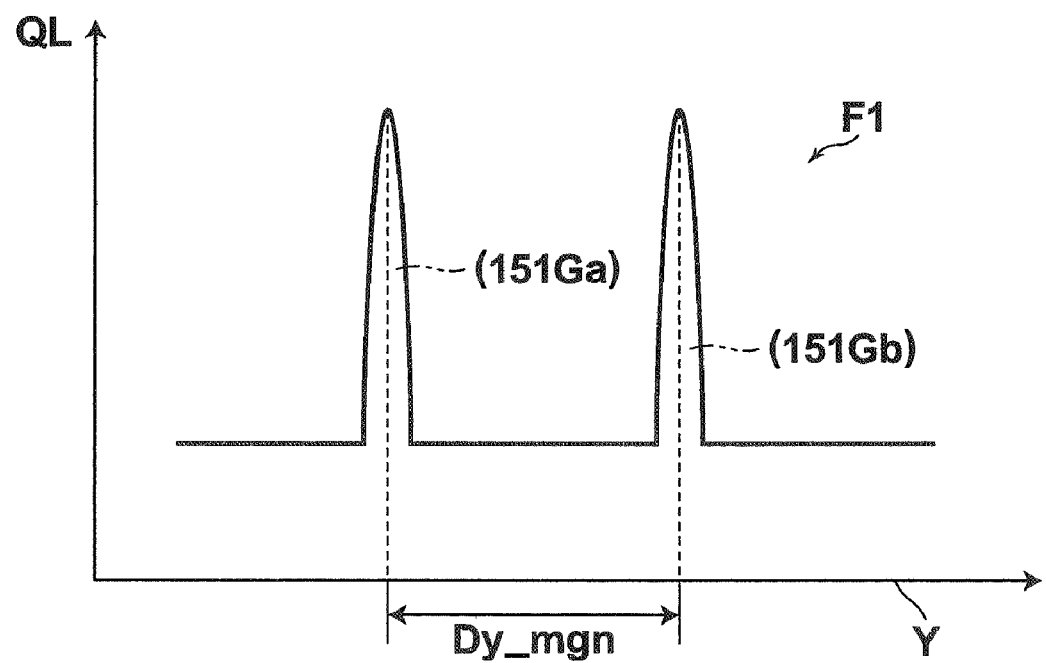

FIGS. 3A and 3B show how the magnification ratio is calculated. FIG. 3A shows a magnification ratio calculation region Ra including images G1 and G2 of the linear components 151A and 151B in the radiation image represented by the image data while FIG. 3B shows profile data F1 generated as a plot of mean values of the image in the magnification ratio calculation region Ra (a two-dimensional region) obtained by averaging pixel values of the image along the X-direction against corresponding values of the Y coordinate (a one-dimensional coordinate). The profile data in FIG. 3B are drawn in a coordinate system whose vertical axis QL and horizontal axis Y respectively represent the pixel values and position along the Y direction. Here, pixel values are values that represent the density of pixels that constitute an image.

[Purpose]

At the time of radiography by the radiography apparatus 200 and at the time of reading by the radiation image reading apparatus 300, the subject is imaged by being enlarged. In other words, the amount of missed tissue at chest wall side calculated from the image data represents a size including the effect of the enlargement. Therefore, the size needs to be converted into an actual size before the enlargement. Consequently, calculation of the magnification ratio of the enlarged image to the actual size is intended.

The magnification ratio is found by using test image data representing the test radiation image obtained by radiography of the phantom 100. The magnification ratio may be found by using the base image data representing the base radiation image.

[Procedures]

Case 1: Calculation of the Magnification Ratio based on Rectangular Piece 161 in the Phantom 100

(1) A size Dy_mgn of the rectangular piece 161 is measured in the Y direction in the image shown by the image data. The size is measured according to a method described in detail in Japanese Unexamined Patent Publication No. 2005-58315.

(2) If the actual size of the rectangular piece 161 is denoted by Dy_nmgn, the magnification ratio can be found by the following equation:

$$Mgn = Dy\_mgn/Dy\_nmgn$$

In the case where the magnification ratio is found respectively for the X direction and for the Y direction, the method described above is used for the rectangular pieces 161 and 162 in the image.

Case 2: Calculation of the Magnification Ratio based on the Two Linear Structures of the Phantom 100 (see FIGS. 3A and 3B)

(1) The profile data F1 (see FIG. 3B) are generated by plotting against the Y coordinate (a one-dimensional coordinate) the mean pixel values obtained through averaging along the X direction the pixel values of the image shown in the magnification ratio calculation region Ra (a two-dimensional region) including images 151Ga and 151Gb (see FIG. 3A) of the linear components 151A and 151B elongated in the X direction in the image represented by the image data.

(2) Peaks corresponding to the two images 151Ga and 151Gb are detected in the profile data F1, and values of the Y coordinate at which the peaks are detected are determined. The distance Dy_mgn is then found between the two peaks in the Y direction. The peaks are found as maximal values in the profile data F1.

For detection of the peaks, see (3) in Step 3 described later.

(3) If an actual distance between the linear components 151A and 151B is denoted by Dy_nmgn, the magnification ratio is found according to the equation below:

$$Mgn = Dy\_mgn/Dy\_nmgn$$

<Step 3: Detection of the Position of the Phantom>

[Purpose]

Position detection of the image representing the phantom 100 is intended based on the coordinates of the reference markers 131 and 132 found at Step 1, at the time of finding the amount of missed tissue at chest wall side by use of the test image data obtained in regular testing.

[Procedures]

(1) The phantom 100 is placed on the support table 210 and radiographed according to regular testing procedures, and the test radiation image of the phantom 100 is recoded in the radiation image conversion panel 1 through the radiography. The radiation image conversion panel 1 having the radiation image of the phantom 100 is then read, and the test image data are obtained comprising digital values representing the outline of the radiation image conversion panel 1 and the radiation image of the phantom 100.

(2) According to the reference marker position detection algorithm described above, the coordinates of the two reference markers 131 and 132 are found by use of the image data, and stored in the missed tissue at chest wall side calculation apparatus 400. The coordinates represent the positions of the reference markers 131 and 132 relative to the outline of the radiation image conversion panel 1.

Let the coordinates of the reference markers 131 and 132 be denoted by (Mdl, Sdl) and (Mdr, Sdr), respectively.

The method described in the paragraphs 0065 to 0089 in Japanese Unexamined Patent Publication No. 2004-298617 can be used as the reference marker position detection algorithm.

(3) By using the coordinates (Mol, Sol) and (Mor, Sor) of the reference markers found at Step 1, deviations in the position of the phantom 100 relative to the support table 210 are found according to the following equation at the time of the testing:

Deviation [mm] in $X$ Direction=$(Mdl-Mol)$*PixSpacing [mm/pix]/$Mgn$

Deviation [mm] in $Y$ Direction=$(Mdl-Mol)$*PixSpacing [mm/pix]/$Mgn$

Rotation [deg] of the Phantom=$\tan^{-1}((Sdl-Sdr)/(Mdl-Mds))$ where Mgn is the magnification ratio found at Step 2, and PixSpacing is a distance between pixels (a sampling interval of the reading apparatus).

The values Mdl, Mol, Sdl, Sol, and the like representing the coordinates correspond to the number of pixels in the corresponding images represented by the image data.

(4) The deviations in X and Y directions found in (3) above are compared with preset permitted values of deviations. In the case where the deviations exceed the permitted values, an error message is displayed. Alternatively, a warning sound is emitted.

<Step 4: Setting of the Calculation Region for Calculation of the Amount of Missed Tissue at Chest Wall Side>

Figure 4A:
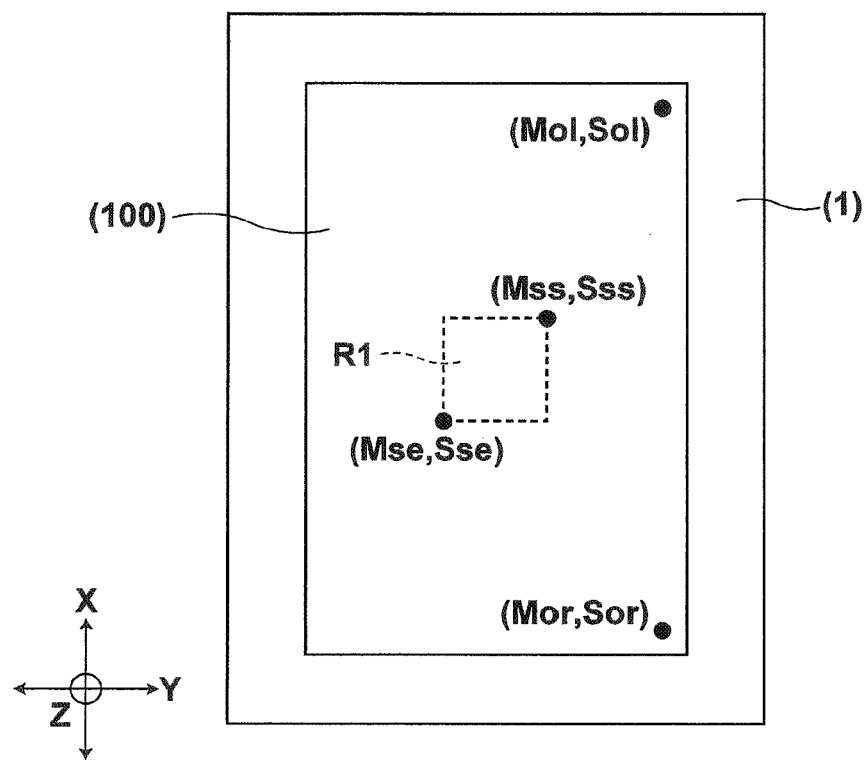
FIGS. 4A and 4B show positions of the phantom and the calculation region relative to a radiation image conversion panel.
Figure 4B:
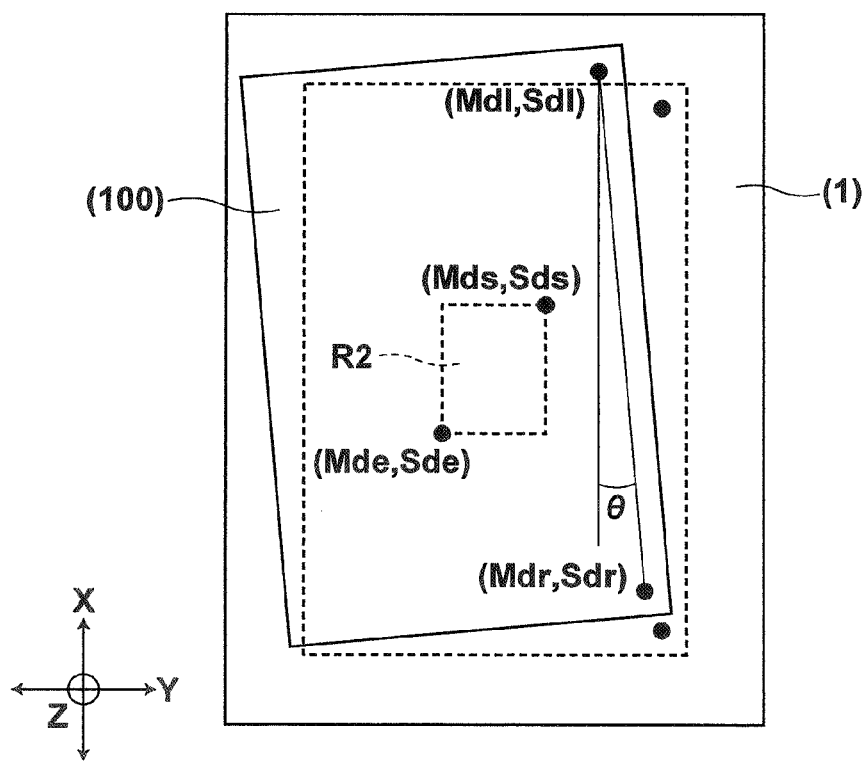

FIGS. 4A and 4B show positions of the phantom and the calculation region relative to the radiation image conversion panel. FIG. 4A shows the positions of the phantom and the calculation region relative to the radiation image conversion panel in the base radiation image while FIG. 4B shows the positions of the phantom and the calculation region relative to the radiation image conversion panel in the test radiation image.

FIGS. 4A and 4B are shown for description of the calculation region setting, and the positional relationship and the like between the phantom and the calculation region are different from other figures that will be described later.

[Purpose]

In the case where the phantom 100 is placed on the support table 210 with a slight positional deviation, the position of the phantom relative to the radiation image conversion panel is deviated. A calculation region R1 for missed tissue at chest wall side calculation is originally set with reference to coordinates of the radiation image conversion panel at the time of base data acquisition, that is, with reference to the outline or the like of the radiation image conversion panel, more specifically.

Therefore, in the case where the phantom 100 is placed on the support table 210 with a slight positional deviation in regular testing, the distance measurement pattern region 140 as the geometric structure for finding the amount of missed tissue at chest wall side may be out of the calculation region determined for the base data acquisition described above. In order to prevent this deviation, correction of the position of the calculation region is intended by use of the coordinates of the reference markers 131 and 132 in the test radiation image.

[Procedures]

(1) Coordinates of the calculation region R1 as a reference are set in advance by use of the base radiation image or the like. In other words, coordinates of a starting point (Mss, Sss) and coordinates of an ending point (Mse, Sse) of the calculation region R1 are stored in advance (see FIG. 4A) in the case of no deviation in the position of the phantom 100 relative to the support table 210.

(2) Coordinates (Mds, Sds) of a starting point and coordinates (Mde, Sde) of an ending point of a calculation region R2 (see FIG. 4B) relative to the test radiation image are found according to the following equations based on the coordinates (Mss, Sss) and (Mse, Sse) of the starting and ending positions of the calculation region R1 and the coordinates (Mol, Sol) and (Mor, Sor) of the reference markers 131 and 132 in the base radiation image with no position deviation (see FIG. 4A) as well as the coordinates (Mdl, Sdl) and (Mdr, Sdr) of the reference markers 131 and 132 in the test radiation image with the position deviations (see FIG. 4B):

$$\begin{pmatrix} Mds \\ Sds \end{pmatrix} = \begin{pmatrix} \cos\theta & -\sin\theta \\ \sin\theta & \cos\theta \end{pmatrix} \begin{pmatrix} Mss - Mol \\ Sss - Sol \end{pmatrix} + \begin{pmatrix} \Delta X \\ \Delta Y \end{pmatrix}$$

$$\begin{pmatrix} Mde \\ Sde \end{pmatrix} = \begin{pmatrix} \cos\theta & -\sin\theta \\ \sin\theta & \cos\theta \end{pmatrix} \begin{pmatrix} Mse - Mol \\ Sse - Sol \end{pmatrix} + \begin{pmatrix} \Delta X \\ \Delta Y \end{pmatrix}$$

$$\theta = \tan^{-1}((Sd1 - Sdr)/(Md1 - Mds))$$

$$\Delta X = Md1 - Mol$$

$$\Delta Y = Sd1 - Sol$$

For the coordinates of the reference markers, see Step 2 and the like above.

<Step 5: Calculation of the Amount of Missed Tissue at Chest Wall Side>

Figure 5A:
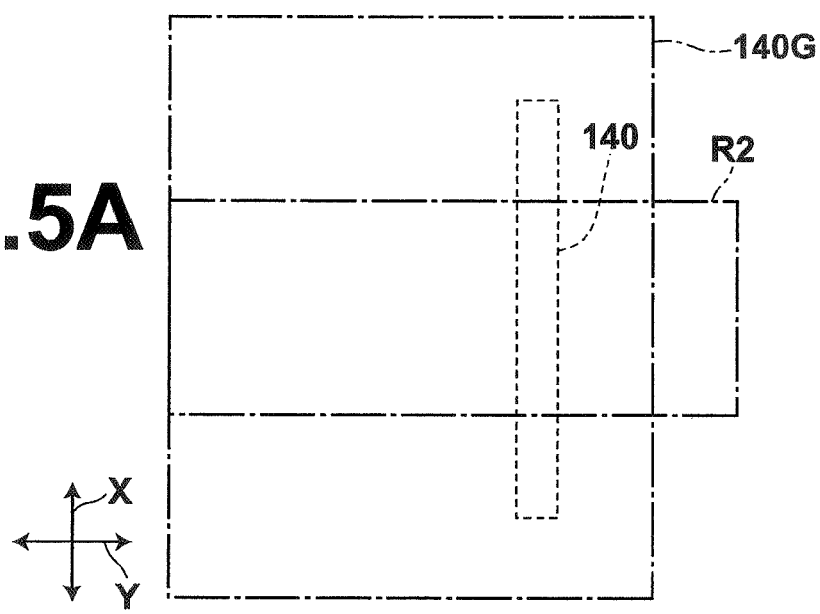
FIGS. 5A to 5C show how profile data are obtained by averaging pixel values of a two-dimensional region along the X direction.
Figure 5B:
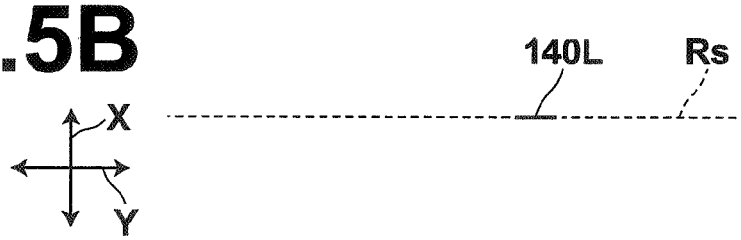
Figure 5C:
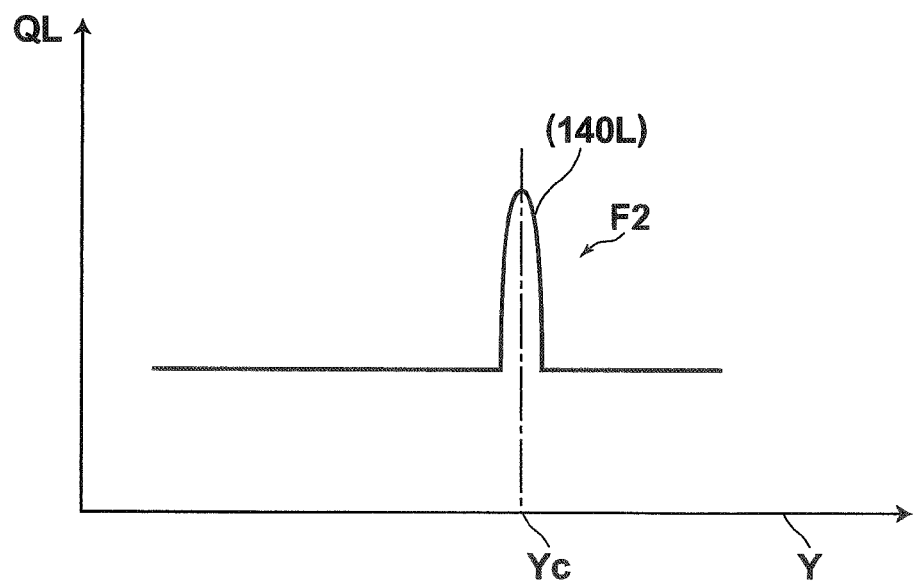

FIGS. 5A to 5C show how profile data that represent average pixel values in a two-dimensional region along the X direction are obtained. FIG. 5A shows the calculation region having been set for a pattern image as an image representing the distance measurement pattern region while FIG. 5B is a diagram of that illustrates the pixel values of a two-dimensional region within the calculation region, which have been averaged along the X direction, along a one-dimensional region Rs that extends in the Y direction. FIG. 5C illustrates a coordinate system having a vertical axis QL for pixel values and a horizontal axis Y for positions in the Y direction, in which profile data that represents the values averaged along the X direction are plotted.

Figure 6A:
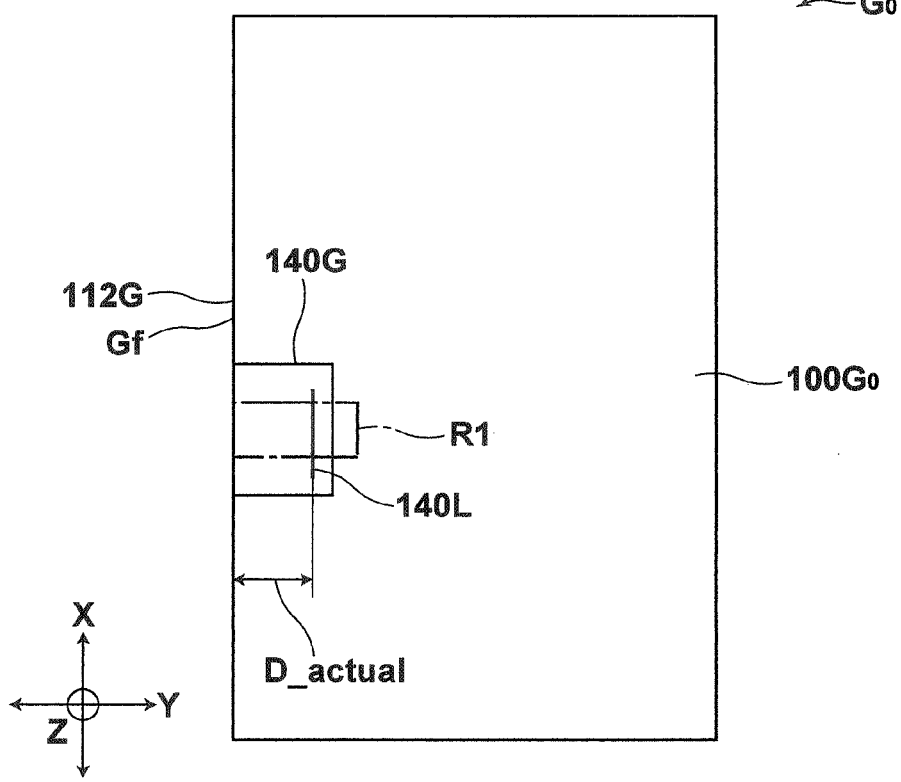
FIGS. 6A and 6B show how an amount of missed tissue at chest wall side is found.
Figure 6B:
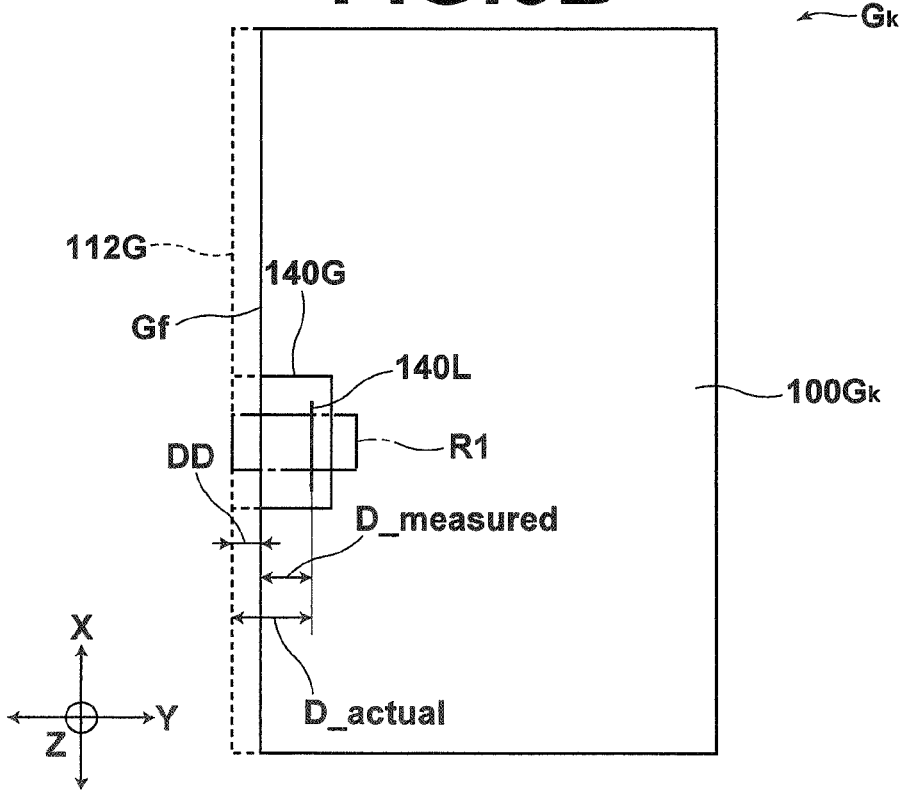

FIGS. 6A and 6B show how the amount of missed tissue at chest wall side is calculated. FIG. 6A shows the image of the phantom in a base radiation image G0 while FIG. 6B shows the image of the phantom in a test radiation image Gk.

[Purpose]

Calculation of the amount of the missed tissue at chest wall side is intended regarding the calculation region R2 found at Step 4 above.

[Procedures]

(1) The test image data are input.

(2) For the calculation region R2 found at Step 4 in the radiation image represented by the image data, the same procedures as for Case 2 in Step 2 are carried out. More specifically, the pixel values of the image in the calculation region R2 (a two-dimensional region) set for a pattern image 140G representing the distance measurement pattern region 140 of the phantom 100 in the test radiation image (see FIG. 5A) are averaged along the X direction and the averaged pixel values (see FIG. 5C) are found along the one-dimensional region Rs in the Y direction (see FIG. 5B). In other words, profile data F2 are found (see FIG. 5C) by plotting against the Y coordinate (one dimension) the mean pixel values obtained by averaging the pixel values of the image in the calculation region R2 along the X direction.

For example, in the case where the distance measurement pattern region 140 has a linear pattern that represents a reference position and is elongated along the X direction, the pattern image 140G has a linear image 140L representing the linear pattern. If the pixel values are averaged along the X direction in the calculation region R2 including the linear image 140L, a region 140L that corresponds to the linear image 140L and has larger pixel values than other regions appears in the profile data F2. The Y coordinate of a center position of the region 140L, which is denoted by Yc, can be determined as a position of the linear image 140L.

In the case where the image data have been obtained after logarithmic conversion, the image data may be inverted into image data represented in the linear space. The method described above can then be applied to the profile data F2.

Before averaging the pixel values in the X direction, median filter processing may be carried out according to a predetermined filter size in order to remove noise in the image represented by the image data.

(3) The amount of missed tissue at chest wall side is calculated from the profile data F2 obtained in the above manner.

As shown in FIG. 6A, a reference line image 112G representing the reference surface 112 appears at a boundary between a radiation field and a non-radiation field in an image 100G0 of the phantom 100 in the base radiation image G0. On the other hand, the reference line image 112G representing the reference surface 112 does not appear in an image 100Gk of the phantom 100 in the test radiation image Gk.

Let D_actual denote a value converted to actual size from a distance between the linear image 140L representing the reference position and the reference line image 112G in the pattern image 140G of the distance measurement pattern region 140 in the base radiation image G0. The position of the linear image 140L can be found by averaging the pixel values in the X direction.

Let an image edge Gf refer to a boundary between the radiation field and the non-radiation field on the side of the reference line image 112G in the test radiation image Gk. Let a value D_measured denote a distance converted to actual size between the image edge Gf and the linear image 140L representing the reference position in the pattern image 140G of the distance measurement pattern region 140 in the test radiation image Gk.

In the test radiation image Gk, a value of the distance converted to actual size between the reference line image 112G that is not shown therein and the linear image 140L is the same as the value D_actual in the base radiation image G0. Therefore, an amount DD of missed tissue at chest wall side is found by DD=D_actual−D_measured.

Hereinafter, the cases will be described where the amount of missed tissue at chest wall side is found by applying the above method to various distance measurement patterns.

<Case 1: The Case where the Distance Measurement Pattern is a Periodically Changing Pattern>

FIGS. 7A and 7B show how the amount of missed tissue at chest wall side is found by using the distance measurement pattern in which the amount of transmitted radiation changes periodically. FIG. 7A shows a calculation region R2 including a pattern image representing the distance measurement pattern region having the periodic amount of transmitted radiation change. FIG. 7B shows periodically changing profile data.

FIG. 7B shows profile data Fa in a coordinate system whose vertical and horizontal axes respectively represent the pixel values and position in the Y direction. The calculation region R2 includes a pattern image 140A representing the pattern region having the periodic amount of transmitted radiation change in the radiation image represented by the image data. The periodically changing profile data Fa represent mean pixel values of the calculation region R2 (a two-dimensional region) obtained by averaging the pixel values therein along the X direction, against the position represented by the Y coordinate.

A coordinate Y0 in FIG. 7B shows a position of the reference line image 112G representing the reference surface 112 of the phantom 100, and a coordinate Y1 shows a position of the image edge Gf as a boundary between an imaged region Ha and a non-imaged region Hb. A coordinate Y2 in FIG. 7B shows a target position in the pattern image 140A of the distance measurement pattern region 140 in the calculation region R2 while a coordinate Y3 represents a position of an edge of the pattern image 140A representing the distance measurement pattern region 140 in the imaged region Ha located on a +Y direction side. A coordinate Y4 represents a position of an edge of the calculation region on the +Y direction side. The +Y direction refers to a direction from the non-imaged region Hb toward the imaged region Ha. The coordinates Y0, Y1, Y2, Y3, and Y4 and the +Y direction denote the same, for Cases 2 and 3 that will be described later.

In the pattern image 140A in the calculation region R2, a region included in the non-imaged region Hb, on which no radiation was irradiated, has not been imaged.

The distance measurement pattern region with the periodic amount of transmitted radiation change can be formed by alternately aligning materials having different amount of transmitted radiations along the Y direction. More specifically, the distance measurement pattern region can be formed by alternately aligning rectangular radiation blocking components A that have a small radiation transmittance and are elongated along the X direction and rectangular radiation blocking components B that have a larger radiation transmittance than the components A and are elongated along the X direction.

Now attention is paid to an image B1 located farthest from the image edge Gf, among images representing the radiation blocking components B forming the periodic pattern. The Y coordinate of a peak corresponding to the image B1 is found in the periodically changing profile data Fa that is a plot of the mean pixel values in the calculation region R2 (a two-dimensional region) obtained by averaging the pixel values in the X direction against the Y coordinate. The Y coordinate representing the peak, that is, a representative position of the image B1, is referred to as the coordinate Y2.

Next is found the Y coordinate of the image edge Gf as the boundary between the imaged region Ha having been exposed to radiation and the non-imaged region Hb not having been exposed to radiation. The Y coordinate of the image edge is referred to as Y1. The imaged region Ha is a region whereon the radiation has been irradiated while the non-imaged region Hb is a region whereon the radiation has not been irradiated.

The actual distance between the coordinate Y0 as the position of the reference line image 112G of the reference surface 112 of the phantom 100 and the coordinate Y2 representing the position of the image B1 is determined at the time of designing of the phantom 100, and is denoted by D_actual. Furthermore, D_measured denotes the actual distance between the coordinate Y1 representing the position of the image edge Gf and the coordinate Y2 representing the position of the image B1, and D_pixmeasured denotes the number of pixels in the image between the coordinate Y1 and the coordinate Y2. The amount DD of missed tissue at chest wall side is calculated according to the following equation.

Amount $DD$ of Missed tissue at chest wall side=$D$_actual−$D$_measured=$D$_actual−($D$_pixmeasured[pix]×PixSpacing[mm/pix]/$Mgn$)

where Mgn is the magnification ratio calculated at Step 2 above and PixSpacing is the distance (the sampling interval of the reading apparatus) between pixels neighboring each other along the Y direction in the image.

How the coordinate Y2 representing the center position of the image B1 showing the radiation blocking component B is calculated will be described below. FIG. 8 shows a method of calculation of the center position in the image representing the component B.

1) A threshold value Thd for profile analysis is calculated according to the following equation:

$Thd = (G\max + G\min)/2$ where Gmax and Gmin respectively represent a maximum value and a minimum value among the pixel values representing the periodic change corresponding to the periodically changing distance measurement pattern region in the periodically changing profile data Fa.

2) As shown in FIG. 8, Y coordinates Sa and Sb and corresponding pixel values QLa and QLb are found for two neighboring pixels A and B sandwiching a line representing the threshold value Thd among pixels representing the periodic change.

3) A Y coordinate S1 at the intersection of the straight line connecting the pixels A and B and the line of the threshold value Thd is found according to the following equation:

$S1 = ((Sa−Sb)/(QLa−QLb))*(Thd−QLa) + Sa$

4) A Y coordinate S2 at the intersection of the line of the threshold value Thd and the straight line connecting two neighboring pixels C and D sandwiching the line representing the threshold value Thd is found in the same manner.

5) A Y coordinate Speak representing the peak described above is the midpoint between the Y coordinate S1 and the Y coordinate S2. Therefore, the coordinate Speak is defined as follows:

$Speak = (S1+S2)/2$

The coordinate Speak corresponds to the coordinate of the edge, that is, Y2 used at the time of finding a value of D_measured.

In this embodiment, the target peak in the periodic change is the peak located farthest from the side of the reference line image 112G (the side of the chest wall). Therefore, the periodically changing profile data Fa are searched from the side opposite of the reference line image 112G in FIG. 7B, and the Y coordinate of the midpoint between the first and second intersections of the profile with the line of the threshold value Thd represents the position of the image B1.

By counting the number of the intersections, the amount DD of missed tissue at chest wall side can be found even if the target peak is set to correspond to any one of the radiation blocking components. In the case where the target peak is the second peak on the side opposite of the reference line image, the Y coordinate of the midpoint between the third and fourth intersections of the profile data and the line of the threshold value Thd becomes the coordinate Speak.

<Case 2: The Case where the Distance Measurement Pattern is a Monotonically Increasing or Decreasing Pattern>

Figure 9A:
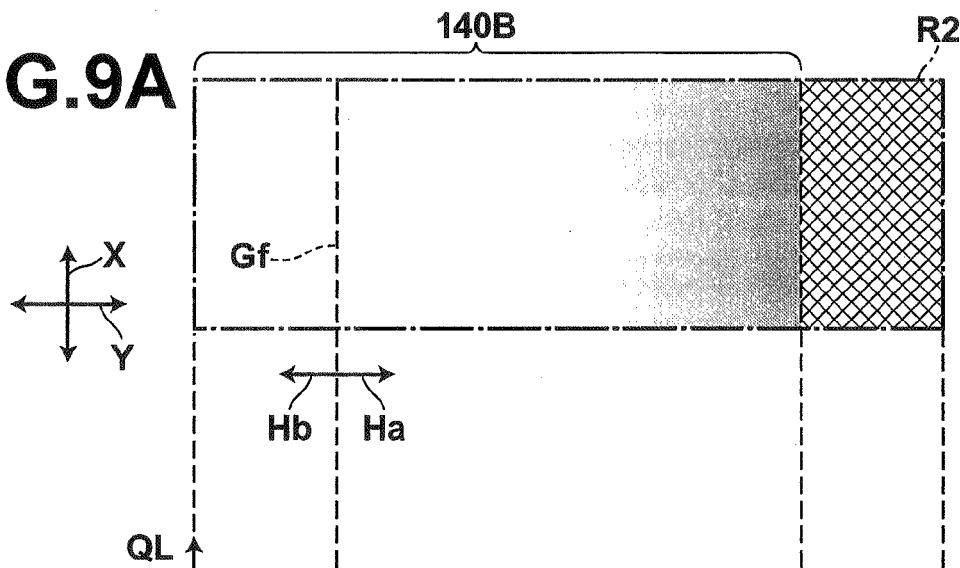
FIGS. 9A and 9B show how the amount of missed tissue at chest wall side is calculated by using a distance measurement pattern in which the amount of transmitted radiation increases monotonically.
Figure 9B:
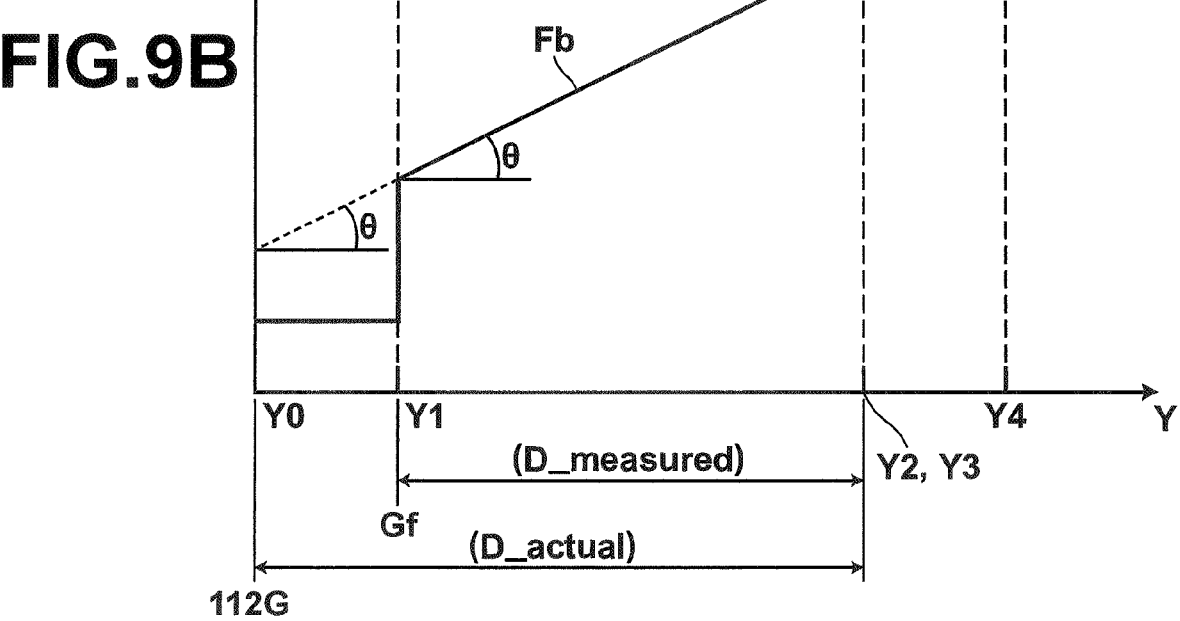

FIGS. 9A and 9B show how the amount of missed tissue at chest wall side is found by using the distance measurement pattern with a monotonically increasing or decreasing amount of transmitted radiation. FIG. 9A shows a calculation region R2 including the distance measurement pattern region with the monotonically increasing amount of transmitted radiation while FIG. 9B shows monotonically increasing profile data.

FIG. 9B shows monotonically increasing profile data Fb in a coordinate system whose vertical and horizontal axes respectively represent the pixel values and position in the Y direction. The calculation region R2 in FIG. 9A includes a pattern image 140B representing the monotonically increasing distance measurement pattern region 140 wherein the amount of transmitted radiation increases monotonically in the radiation image represented by the image data. The monotonically increasing profile data Fb shows a plot of the mean pixel values of the calculation region R2 (a two-dimensional region) obtained by averaging the pixel values in the X direction against the Y coordinate.

Below will be described the case where the distance measurement pattern region 140 is a region wherein the amount of transmitted radiation increases monotonically, that is, a region having a material whose thickness increases monotonically in the +Y direction.

An angle θ of inclination is found in advance between a distance in the Y direction between positions at which the amount of transmitted radiation becomes largest and smallest in the monotonically increasing distance measurement pattern region 140 in the phantom 100 and a change in the amount of transmitted radiation along the distance. In other words, the angle θ is found in advance between an increase in the Y coordinate in the radiation image of the monotonically increasing distance measurement pattern region 140 and an increase in the pixel values of the radiation image.

The monotonically increasing profile data Fb, in which the amount of transmitted radiation increases monotonically with an increase in the Y coordinate, are then analyzed. The amount DD of missed tissue at chest wall side is found according to the following equation, based on a pixel value QL_edge at the position Y1 representing the image edge Gf as the boundary between the imaged region Ha having been exposed to radiation and non-imaged region Hb not having been exposed to radiation and based on a pixel value QL_ave at the position Y2 at which the amount of transmitted radiation becomes largest in the pattern image 140B representing the monotonically increasing distance measurement region 140:

$DD = D\_actual − D\_measured = D\_actual − (QL\_ave − QL\_edge)(1/\tan θ) × PixSpacing[mm/pix]/Mgn$ where the angle θ is the angle of inclination determined at the time of designing of the phantom 100, Mgn is the magnification ratio found at Step 2, and PixSpacing is the distance between neighboring pixels in the Y direction (the sampling interval of the reading apparatus).

The method described above can also be applied to the case where the amount of transmitted radiation decreases monotonically in the distance measurement pattern region 140.

<Case 3: The Case where the Pattern Changes in a Stepwise Manner>

Figure 10A:
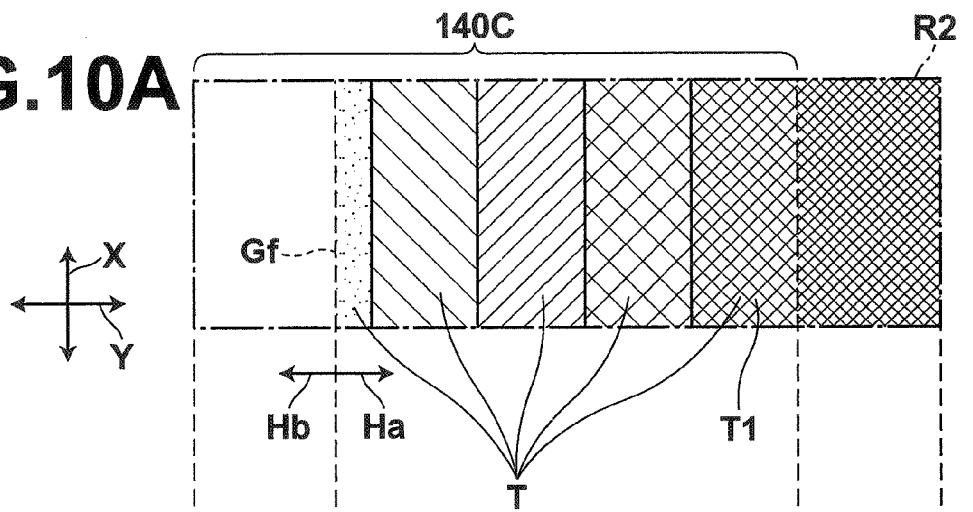
FIGS. 10A and 10B show how the amount of missed tissue at chest wall side is found by using a distance measurement pattern wherein the amount of transmitted radiation changes in a stepwise manner.
Figure 10B:
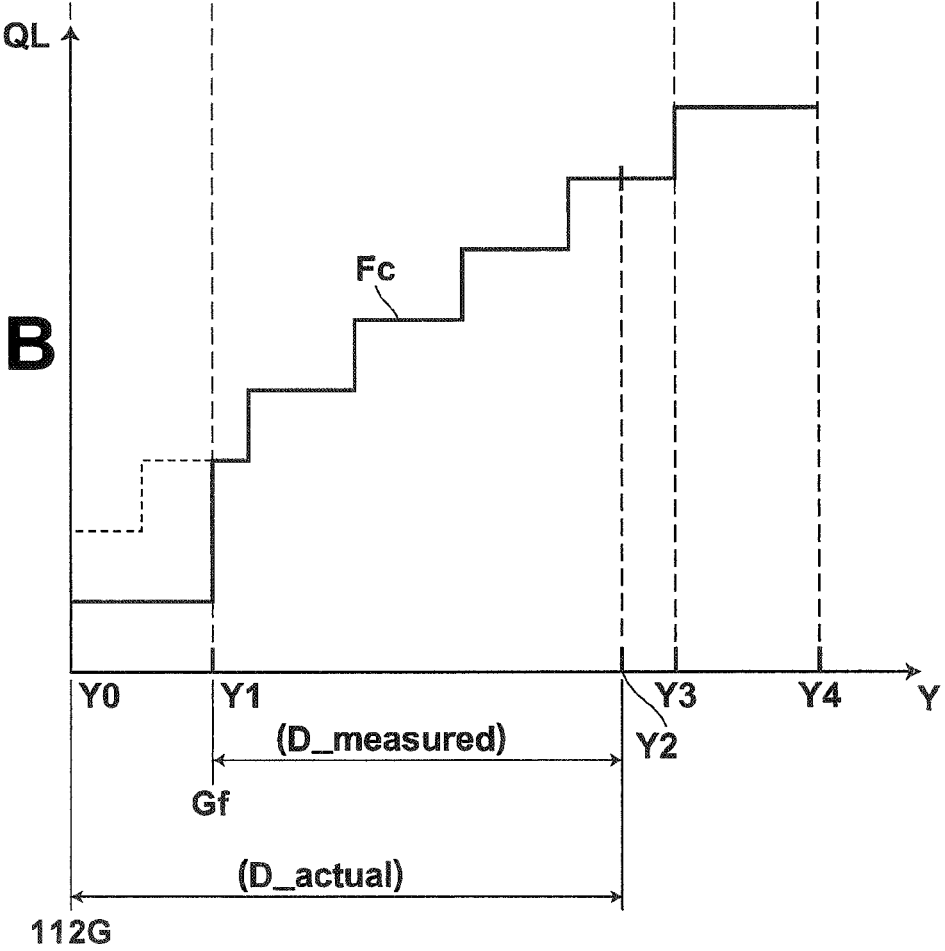

FIGS. 10A and 10B show how the amount of missed tissue at chest wall side is found by use of the distance measurement pattern in which the amount of transmitted radiation changes in a stepwise manner. FIG. 10A shows a calculation region R2 including an image of the distance measurement pattern region having the amount of transmitted radiation of stepwise change while FIG. 10B shows stepwise profile data. FIGS. 11A and 11B show how a center position of a step is found by differentiation of the stepwise profile data. FIG. 1A shows the stepwise profile data before the differentiation and FIG. 11B shows differentiated stepwise profile data.

FIGS. 10B and 11A show profile data Fc in a coordinate system whose vertical and horizontal axes respectively represent the pixel values and position along the Y direction. The calculation region R2 in FIG. 10A includes a pattern image 140C representing the stepwise distance measurement pattern region 140 in which the amount of transmitted radiation changes in a stepwise manner in the radiation image represented by the image data. The stepwise profile data Fc show a plot of the mean pixel values of the calculation region R2 (a two-dimensional region) obtained by averaging the pixel values therein along the X direction against the Y coordinate.

Hereinafter, the case where the distance measurement pattern region 140 is a region in which the amount of transmitted radiation changes in a stepwise manner will be described. More specifically will be described the case where a material whose thickness changes in a stepwise manner in the +Y direction is laid out in the distance measurement pattern region 140 to cause the stepwise changes in the amount of transmitted radiation.

Attention is paid to a target step that is located farthest from the reference line image 112G representing the reference surface 112 of the phantom 100, among steps T of the pattern region. The Y coordinate representing a center of an image T1 of the target step is referred to as the coordinate Y2.

The Y coordinate of the image edge Gf as the boundary between the imaged region Ha having been exposed to radiation and the non-imaged region Hb not having been exposed to radiation is then found. This Y coordinate is referred to as Y1.

The actual distance between the coordinate Y0 as the position of the reference line image 112G of the reference surface 112 of the phantom 100 and the coordinate Y2 representing the position of the image T1 is determined at the time of designing of the phantom 100, and is denoted by D_actual.

Furthermore, D_measured denotes the actual distance between the coordinate Y1 representing the position of the image edge Gf and the coordinate Y2 representing the position of the image T1, and D_pixmeasured denotes the number of pixels in the image between the coordinate Y1 and the coordinate Y2. The amount DD of missed tissue at chest wall side is calculated according to the following equation.

$$DD = D\_actual - D\_measured = D\_actual - (D\_pixmeasured[pix] \times PixSpacing[mm/pix]/Mgn)$$

where Mgn is the magnification ratio calculated at Step 2 above and PixSpacing is the distance (the sampling interval of the reading apparatus) between pixels neighboring each other along the Y direction in the image.

Hereinafter, how the coordinate Y2 of the center of the image T1 representing the target step is found will be described with reference to FIGS. 11A and 11B.

1) The stepwise profile data Fc are differentiated (differences between neighboring pixels are found).

Let P(i) denote the pixel value of the stepwise profile data Fc. A pixel value of differentiated profile data Fc' can be found according to the following equation:

$$P'(i) = P(i) - P(i-1)$$

2) A midpoint between peaks in the differentiated profile data Fc' shown in FIG. 11B is a coordinate (Sstep) of the center. Therefore, positions of the peaks are calculated in the differentiated profile data Fc' according to the method of peak detection described in Case 1 above, and the midpoint between the peaks can be found as the coordinate of the center of the image T1 of the target step.

<Step 5': Addition to Step 5: Finding the Amount of Missed Tissue at Chest Wall Side by Excluding a White Region>

[Purpose]

If the radiation image conversion panel 1 is a stimulable phosphor sheet and the radiation image reading apparatus 300 reads the radiation image recorded in the stimulable phosphor sheet while conveying the sheet, an image region in which pixel values are 0 (hereinafter referred to as a white region) may be generated in the case where the sheet has not been conveyed straightly and thus a region where the sheet does not exist has been read. In the case where the white region is on the side of the reference line image 112G representing the reference surface 112 of the phantom 100, the white region may be included for calculation of the amount of missed tissue at chest wall side. Therefore, calculation of the amount excluding the white region is intended.

[Procedures]

(1) According to 1) to 3) of Step 5 above, the stepwise profile data Fc are found.

(2) The stepwise profile data Fc are searched from the side opposite of the reference line image 112G, and a coordinate S_white representing a position in the Y coordinate, at which the pixel value becomes smaller for the first time than a threshold value Thd_white used for detecting the white region, is found.

The threshold value Thd_white is a fixed value and given as a parameter in advance.

(3) In calculation of the amount of missed tissue at chest wall side in the Cases 1, 2, and 3 above, if the white region is included in the amount of missed tissue at chest wall side, the amount DD of missed tissue at chest wall side can be calculated by excluding the white region according to the coordinate S_white:

$$DD = D\_actual - (D\_pixmeasured - S white) * PixSpacing [mm/pix]/Mgn$$

where D_actual, D_pixmeasured, PixSpacing, and Mgn are the same as in Cases 1 to 3 above.

<Step 6: Judgment on the Amount of Missed Tissue at Chest Wall Side>

[Purpose]

An automatic judgment on a result of calculation of the amount of missed tissue at chest wall side and warning are intended.

[Procedures]

The calculated amount of missed tissue at chest wall side is compared with a preset judgment criterion and whether the amount is within the permitted range is judged. If a result of the judgment is negative, warning is carried out.

What is claimed is:

1. A method for measuring an amount of missed tissue at chest wall side, the method comprising the steps of:

placing a phantom used for measurement of the amount of missed tissue at chest wall side on a support table for breast radiography, the phantom comprising a reference marker located at a predetermined position in the phantom, a reference surface for positioning, to be placed in contact with a chest wall side of the support table, and a pattern region formed by a region wherein the amount of transmitted radiation used for measurement of a distance from the reference surface shows periodic changes, monotonic decrease or increase, or stepwise changes in a direction perpendicular to the reference surface according to a predetermined rule;

recording a radiation image of the phantom in a radiation image conversion panel placed in the support table while radiographing the phantom;

obtaining base image data representing a base radiation image of the phantom including the reference marker by performing readout of the radiation image conversion panel;

finding a magnification ratio and a position of the phantom from a test radiation image obtained by further radiography of the phantom and from a position of the reference marker recorded in the test radiation image;

determining a calculation region corresponding to the pattern region in the test radiation image, based on the position of the phantom and the base image data;

finding the number of repetitions and/or the amount of change in the amount of transmitted radiation in the calculation region according to the predetermined rule; and finding the amount of missed tissue at chest wall side from the number of repetitions and/or the amount of the change.

2. The method according to claim 1 for measuring the amount of missed tissue at chest wall side, the method further comprising the steps of:

comparing the amount of missed tissue at chest wall side with a predetermined permitted amount of missed tissue at chest wall side; and issuing a warning in the case where the amount of missed tissue at chest wall side has been judged to exceed the permitted amount of missed tissue at chest wall side.

3. A method for measuring an amount of missed tissue at chest wall side, the method comprising the steps of:

correctly placing a phantom used for measurement of the amount of missed tissue at chest wall side on a support table for breast radiography, the phantom comprising a reference marker located at a predetermined position in the phantom, a reference surface for positioning, to be placed in contact with a chest wall side of the support table, and a pattern region formed by a region wherein the amount of transmitted radiation used for measurement of a distance from the reference surface shows periodic changes, monotonic decrease or increase, or stepwise changes in a direction perpendicular to the reference surface according to a predetermined rule;

recording a radiation image of the phantom, which has been correctly placed on the support table, in a radiation image conversion panel placed in the support table by performing radiography;

obtaining a base radiation image that represents the positional relationship between the reference marker and the radiation image conversion panel when the phantom is correctly placed on the support table, by performing readout of the radiation image conversion panel;

placing the phantom on the support table;

recording a radiation image of the phantom in the radiation image conversion panel, which is correctly placed in the support table, by performing radiography;

obtaining an examination radiation image that represents the positional relationship between the reference marker and the radiation image conversion panel when the radiation image conversion panel is correctly placed in the support table, by performing readout of the radiation image conversion panel;

comparing the base radiation image and the examination radiation image, to obtain the difference in the positional relationships between the reference marker and the radiation image conversion panel when the phantom is correctly placed on the support table and when the radiation image conversion panel is correctly placed in the support table; and correcting the position of a lost region within the distance measuring pattern region, which is not recorded within the examination radiation image, an amount corresponding to the difference in the positional relationships, to obtain the amount of missed tissue at chest wall side.

4. A phantom placed on a support table for breast radiography and used for measurement of an amount of missed tissue at chest wall side, the phantom comprising:

a reference marker located at a predetermined position in the phantom;

a reference surface for positioning, the surface in contact with a chest wall side of the support table; and a pattern region used for measurement of a distance from the reference surface and formed by a region wherein the amount of transmitted radiation changes in a direction perpendicular to the reference surface according to a predetermined rule, wherein the pattern region is an alternating geometric structure for forming a predetermined radiation image from a boundary of the missed tissue of the chest wall side to the reference marker disposed opposite to the chest wall side.

5. The phantom according to claim 4 wherein the pattern region for measurement of the distance is a region wherein the amount of transmitted radiation decreases or increases monotonically.

6. The phantom according to claim 4 wherein the pattern region for measurement of the distance is a region wherein the amount of transmitted radiation changes in a stepwise manner.

7. The phantom according to claim 4, wherein the pattern region is formed in a support region of the phantom is present in a radiation field upon imaging of a body part.

8. The phantom according to claim 4, wherein the chest wall side of the support table is the surface of the support table that is in contact with a chest wall of a subject.

9. The phantom according to claim 4, wherein the positioning of the reference surface allows for measuring the amount of missed tissue at the chest wall side.

* * * * *